(12) United States Patent
Hara et al.

(10) Patent No.: US 12,020,826 B2
(45) Date of Patent: Jun. 25, 2024

(54) PATHOGEN DISTRIBUTION INFORMATION PROVISION SYSTEM, PATHOGEN DISTRIBUTION INFORMATION PROVISION SERVER, AND METHOD FOR PROVIDING PATHOGEN DISTRIBUTION INFORMATION

(71) Applicant: Panasonic Intellectual Property Management Co., Ltd., Osaka (JP)

(72) Inventors: Kohei Hara, Osaka (JP); Akiko Murata, Osaka (JP); Tetsuya Takayanagi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1029 days.

(21) Appl. No.: 16/918,000

(22) Filed: Jul. 1, 2020

(65) Prior Publication Data
US 2020/0335226 A1 Oct. 22, 2020

Related U.S. Application Data

(63) Continuation of application No. PCT/JP2019/014630, filed on Apr. 2, 2019.

(30) Foreign Application Priority Data

Apr. 27, 2018 (JP) ................. 2018-086491

(51) Int. Cl.
| | |
|---|---|
| G01N 33/48 | (2006.01) |
| G01N 33/569 | (2006.01) |
| G06F 15/00 | (2006.01) |
| G16B 45/00 | (2019.01) |
| G16H 50/30 | (2018.01) |
| G16H 50/50 | (2018.01) |
| G16H 50/80 | (2018.01) |
| G16H 70/60 | (2018.01) |

(52) U.S. Cl.
CPC ....... *G16H 50/80* (2018.01); *G01N 33/56983* (2013.01); *G16B 45/00* (2019.02); *G16H 50/30* (2018.01); *G16H 50/50* (2018.01); *G16H 70/60* (2018.01)

(58) Field of Classification Search
None
See application file for complete search history.

(56) References Cited

U.S. PATENT DOCUMENTS

| | | |
|---|---|---|
| 2014/0046722 A1 | 2/2014 | Rosenbloom et al. |
| 2016/0306934 A1 | 10/2016 | Sperry et al. |
| 2017/0322682 A1 | 11/2017 | Humayun et al. |

FOREIGN PATENT DOCUMENTS

| | | |
|---|---|---|
| JP | 2005-275708 | 10/2005 |
| JP | 2009-271326 | 11/2009 |
| JP | 2013-190875 | 9/2013 |

OTHER PUBLICATIONS

Usachev, Evgeny V., et al. "Portable automatic bioaerosol sampling system for rapid on-site detection of targeted airborne microorganisms." Journal of Environmental Monitoring 14.10 (2012): 2739-2745.*
Lee, Joonhyung, et al. "Real-time detection of airborne viruses on a mass-sensitive device." Applied Physics Letters 93.1 (2008).*
Takenaka, Kei, et al. "Airborne virus detection by a sensing system using a disposable integrated impaction device." Journal of Breath Research 10.3 (2016): 036009.*
Yang, Wan, Subbiah Elankumaran, and Linsey C. Marr. "Concentrations and size distributions of airborne influenza A viruses measured indoors at a health centre, a day-care centre and on aeroplanes." Journal of the Royal Society Interface 8.61 (2011): 1176-1184.*
International Search Report of PCT application No. PCT/JP2019/014630 dated Jun. 25, 2019.
Takashi Kurabuchi et al., "Relationship between Absolute Humidity and Virus Survival Rate Affecting Influenza Transmission", Technical Papers of Annual Meeting, The Society of Heating, Air-Conditioning Sanitary Engineers of Japan, Sep. 15, 2009, pp. 1339-1342.
G. J. Harper, "Airborne micro-organisms: survival tests with four viruses", J. Hyg., Camb. (1961), 59, Dec. 1961, pp. 479-486.
Makoto Shoji, "Correlation between seasons and influenza epidemics", J. Natl. Inst. Public Health, vol. 48(4), 1999, pp. 282-290.
Extended European Search Report issued May 11, 2021 in corresponding European Patent Application No. 19791487.2.

* cited by examiner

*Primary Examiner* — Anna Skibinsky
(74) *Attorney, Agent, or Firm* — Wenderoth, Lind & Ponack, L.L.P.

(57) ABSTRACT

An infection risk map provision system includes virus sensors for detecting viruses in the air, the virus sensors being provided at different positions, a communication unit that collects detection information obtained by the virus sensors, and a control unit that provides, on the basis of the detection information, an infection risk map representing the distribution of infection risk information. The control unit sets display granularity for the infection risk information on the infection risk map displayed on an information terminal on the basis of granularity information corresponding to the virus sensors and creates the infection risk map by superimposing the infection risk information upon a map on the basis of the set display granularity and positional information.

14 Claims, 14 Drawing Sheets

FIG. 3

DEVICE ID: VS1234567
DATE: 01/20/2018

| TIME | VIRUS | POSITION | TEMPERATURE | HUMIDITY | HUMAN |
|---|---|---|---|---|---|
| 7:00 | — | | 10 | 30 | — |
| 8:00 | — | | 10 | 30 | — |
| 9:00 | H | LATITUDE...<br>LONGITUDE... | 15 | 35 | CROWDED |
| 10:00 | H | | 17 | 25 | CROWDED |
| 11:00 | L | LATITUDE...<br>LONGITUDE... | 17 | 25 | — |
| 12:00 | L | | 20 | 60 | — |
| 13:00 | — | | 20 | 60 | — |
| ⋮ | ⋮ | ⋮ | ⋮ | ⋮ | ⋮ |

FIG. 4

DATE: 01/20/2018

| TIME | DEVICE ID | VIRUS | POSITION | TEMPERATURE [°C] | RELATIVE HUMIDITY [%] | ABSOLUTE HUMIDITY [g/m³] | PREVALENCE LEVEL | HUMAN | ALLOWABLE LOWER-LIMIT GRANULARITY LEVEL | INFECTION RISK |
|---|---|---|---|---|---|---|---|---|---|---|
| 9:00 | VS1234567 | – | LATITUDE... LONGITUDE... | 15 | 35 | 4.6 | WARNING | CROWDED | 1 | CAUTION |
| 9:00 | VS1234569 | L | LATITUDE... LONGITUDE... | 20 | 60 | 10.3 | CAUTION | | 2 | CAUTION |
| 9:05 | VS1323456 | H | LATITUDE... LONGITUDE... | 15 | 35 | 4.6 | WARNING | CROWDED | 3 | DANGER |
| 9:06 | VS1523456 | – | LATITUDE... LONGITUDE... | 20 | 60 | 10.3 | | CROWDED | 3 | SAFE |
| 9:20 | VS1789123 | L | LATITUDE... LONGITUDE... | 17 | 40 | 5.8 | CAUTION | | 2 | DANGER |
| 9:25 | VS1234789 | – | LATITUDE... LONGITUDE... | 20 | 50 | 8.6 | | CROWDED | 3 | SAFE |
| 9:25 | VS1645612 | H | LATITUDE... LONGITUDE... | 20 | 60 | 10.3 | WARNING | | 1 | DANGER |
| ⋮ | ⋮ | ⋮ | ⋮ | ⋮ | ⋮ | ⋮ | ⋮ | ⋮ | ⋮ | ⋮ |

FIG. 5

| GRANULARITY LEVEL | GRANULARITY (RANGE) |
|---|---|
| 1 | ROOM |
| 2 | BUILDING |
| 3 | AREA |
| 4 | CITY, WARD, TOWN, VILLAGE |
| 5 | PREFECTURE |

PATHOGEN DISTRIBUTION INFORMATION PROVISION SYSTEM, PATHOGEN DISTRIBUTION INFORMATION PROVISION SERVER, AND METHOD FOR PROVIDING PATHOGEN DISTRIBUTION INFORMATION

BACKGROUND

1. Technical Field

The present disclosure relates to a pathogen distribution information provision system and the like that provide pathogen distribution information representing the distribution of pathogen information at different positions.

2. Description of the Related Art

As a system that reports virus propagation information in order to prevent infection with influenza, there is currently a system that accumulates influenza information obtained by medical facilities, public institutions, or personal mobile information terminals equipped with a cold virus detection device and that widely reports the information over a communication network (refer to Japanese Unexamined Patent Application Publication No. 2005-275708).

In Japanese Unexamined Patent Application Publication No. 2005-275708, mobile information terminals equipped with a cold virus propagation information transmission device, medical facility terminals, and public institution terminals transmit cold virus information to a cold virus information center apparatus over a communication network. The cold virus information center apparatus then transmits cold virus propagation information to each terminal over the communication network.

In addition, there is a technique for providing information with which a geographical progression direction of prevalence of a cold can be estimated by mapping information regarding human body temperature onto a map and visually representing the distribution of patients who have developed a fever (refer to Japanese Unexamined Patent Application Publication No. 2013-190875).

SUMMARY

In the above examples of the related art, however, various pieces of information are created on the basis of information regarding patients who have developed symptoms after infection. In Japanese Unexamined Patent Application Publication No. 2005-275708, for example, information is created on the basis of patients who have developed symptoms and seen a doctor. In addition, in Japanese Unexamined Patent Application Publication No. 2013-190875, for example, information is created on the basis of patients who have developed a fever. Information, therefore, cannot be obtained until infected persons develop symptoms of a disease, and information regarding infection is not collected promptly. In addition, because there are diseases contagious between infection and development of symptoms (i.e., during an incubation period), provided information alone is not enough to prevent infection.

One non-limiting and exemplary embodiment provides a pathogen distribution information provision system and the like capable of promptly providing information beneficial to prevention of infection.

In one general aspect, the techniques disclosed here feature a pathogen distribution information provision system according to an aspect of the present disclosure includes pathogen detectors for detecting a pathogen in air, the pathogen detectors being provided at different positions, a communicator that collects, over a communication network, detection information obtained by the pathogen detectors, a storage that stores the collected detection information and positional information regarding the pathogen detectors while associating the detection information and the positional information with each other, and a controller that provides pathogen distribution information indicating distribution of pathogen information for an information terminal through the communicator on a basis of the detection information stored in the storage. The controller sets, on a basis of granularity information corresponding to the pathogen detectors, display granularity for the pathogen information in the pathogen distribution information displayed on the information terminal and creates the pathogen distribution information by superimposing the pathogen information upon a map on a basis of the set display granularity and the positional information.

With the pathogen distribution information provision system according to the aspect of the present disclosure, information beneficial to prevention of infection can be promptly provided.

It should be noted that this general or specific aspect may be implemented as an apparatus, a method, an integrated circuit, a computer program, a computer-readable storage medium, or any selective combination of an apparatus, a system, a method, an integrated circuit, a computer program, and a computer-readable storage medium. The computer-readable storage medium may be, for example, a nonvolatile storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a diagram illustrating an example of detection information according to the embodiment;

FIG. 4 is a diagram illustrating an example of information regarding evaluation of an infection risk according to the embodiment;

FIG. 5 is a diagram illustrating an example of granularity levels according to the embodiment;

DETAILED DESCRIPTION

Figure 1:
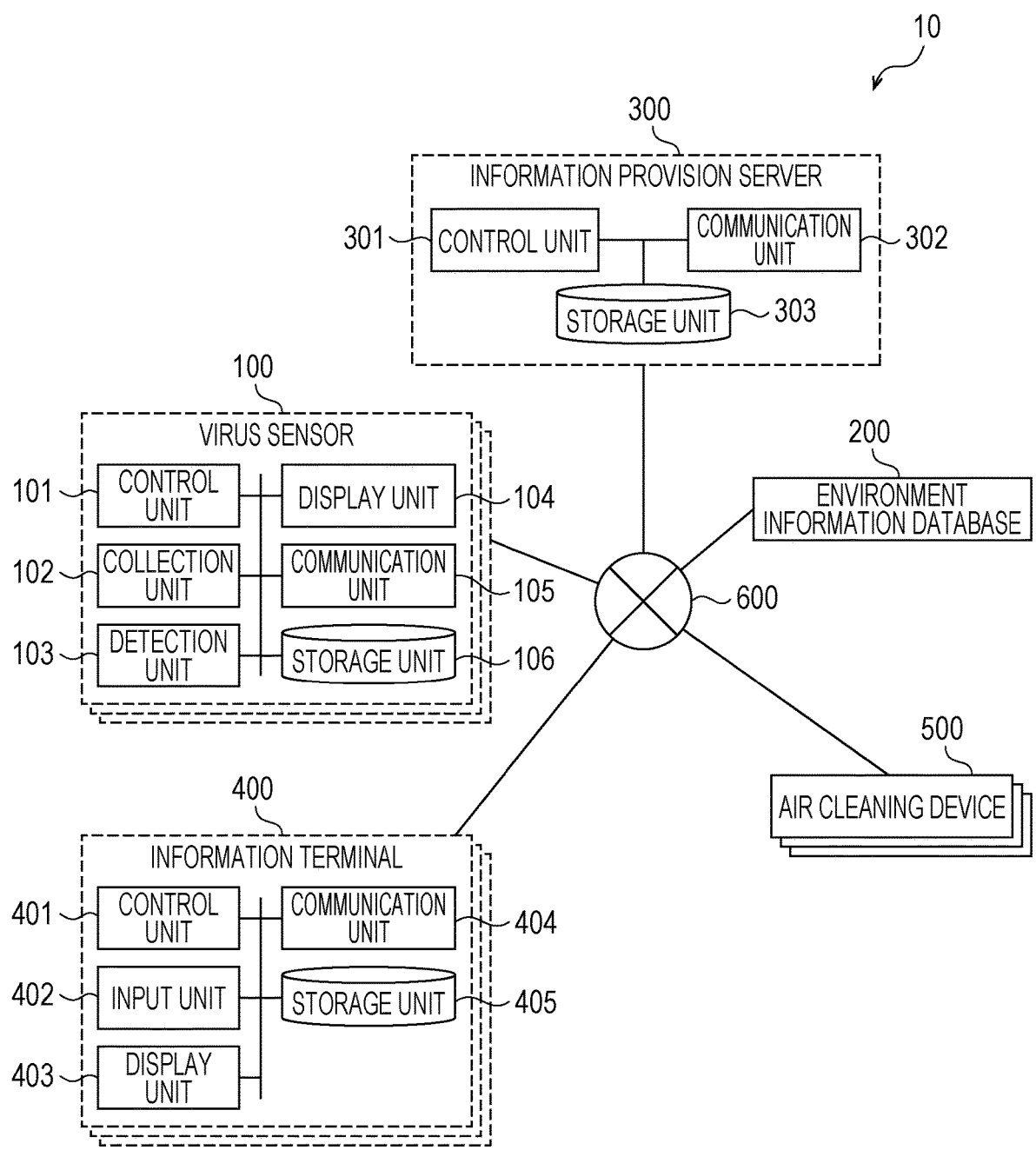
FIG. 1 is a block diagram illustrating the functional configuration of an infection risk map provision system according to an embodiment.

Underlying Knowledge Forming Basis of Present Disclosure

It is possible that detection information regarding viruses is collected using influenza virus sensors provided at eldercare facilities, medical facilities, and the like in order to collect information regarding viruses before development of symptoms. By sharing such detection information on a network, information beneficial to prevention of infection can be provided promptly. Furthermore, virus distribution information can be visually provided by mapping the detection information onto a map.

When virus distribution information is provided in such a manner, it is usually desirable to provide the virus distribution information with finer granularity. If detection information regarding viruses is provided with positions at which virus sensors are provided being identifiable, however, privacy information regarding infection of managers of the virus sensors and the like is undesirably disclosed. In addition, when a virus sensor is provided in a restaurant, a retail shop, or the like, the number of customers of the store might significantly decrease if a position at which the virus sensor is provided is identified. Managers of virus sensors, therefore, might be hesitant about setting the virus sensors and providing detection information.

In order to promote setting of virus sensors and provision of detection information, therefore, privacy of managers of the virus sensors and the like need to be protected.

A pathogen distribution information provision system according to an aspect of the present disclosure therefore includes pathogen detectors for detecting a pathogen in air, the pathogen detectors being provided at different positions, a communicator that collects, over a communication network, detection information obtained by the pathogen detectors, a storage that stores the collected detection information and positional information regarding the pathogen detectors while associating the detection information and the positional information with each other, and a controller that provides pathogen distribution information indicating distribution of pathogen information for an information terminal through the communicator on a basis of the detection information stored in the storage. The controller sets, on a basis of granularity information corresponding to the pathogen detectors, display granularity for the pathogen information in the pathogen distribution information displayed on the information terminal and creates the pathogen distribution information by superimposing the pathogen information upon a map on a basis of the set display granularity and the positional information.

According to this, the detection information obtained by the pathogen detector can be collected, and the pathogen distribution information representing the distribution of the pathogen information can be provided for the information terminal on the basis of the detection information. The pathogen distribution information, therefore, can reflect the pathogen information more promptly than in the examples of the related art, in which information is not obtained until patients who have developed symptoms of a disease caused by a pathogen see a doctor. As a result, information beneficial to prevention of infection from not only patients who have developed symptoms but also patients who have not developed symptoms yet can be provided, and information beneficial to prevention of infection can be provided promptly.

Furthermore, the display granularity for the pathogen information in the pathogen distribution information can be set on the basis of the granularity information corresponding to the pathogen detectors. The display granularity for the pathogen information, therefore, can be adjusted for each of the pathogen detectors. That is, when a manager of a pathogen detector does not desire a position at which the pathogen detector is provided to be identified from the pathogen distribution information, display granularity for pathogen information corresponding to the pathogen detector can be made coarse, and privacy of the manager of the pathogen detector and the like can be protected.

In addition, in the pathogen distribution information provision system according to the aspect of the present disclosure, in the creation of the pathogen distribution information, the controller may inhibit, for the pathogen information, superimposition of the pathogen information upon the map in an area having a size smaller than a size of an area on the map indicated by the granularity information.

According to this, the superimposition of the pathogen information in the area on the map having a size smaller than the size of the area on the map indicated by the granularity information can be inhibited. The size of the area in which the pathogen information is superimposed, therefore, is prevented from becoming too small, and privacy of the managers of the pathogen detectors and the like can be protected more securely.

In addition, in the pathogen distribution information provision system according to the aspect of the present disclosure, the pathogen detectors may include a first pathogen detector provided at a first position. The detection information may include first detection information obtained by the first pathogen detector. The storage may store first granularity information indicating first allowable lower-limit granularity while associating the first granularity information with the first pathogen detector. If the communicator receives, from the information terminal, a request for first pathogen distribution information on a first map on a first scale and the first map includes the first position, the controller may (i) obtain first predetermined granularity corresponding to the first map, (ii-1) set, if the first predetermined granularity is equal to or higher than the first allowable lower-limit granularity, the first predetermined granularity as first display granularity for first pathogen information based on the first detection information, (ii-2) set, if the first predetermined granularity is lower than the first allowable lower-limit granularity, the first allowable lower-limit granularity as the first display granularity, and (iii) create the first pathogen distribution information by superimposing the first pathogen information in a first area, which has a first size corresponding to the set first display granularity and is located at the first position on the first map.

According to this, when the first predetermined granularity corresponding to the first map is used as default display granularity, the first display granularity can be prevented from becoming lower than the first allowable lower-limit granularity, and privacy of a manager of the first pathogen detector and the like can be protected more securely on the first map.

In addition, in the pathogen distribution information provision system according to the aspect of the present disclosure, the pathogen detectors may further include a second pathogen detector provided at a second position. The detection information may include second detection information obtained by the second pathogen detector. The storage may also store second granularity information indicating second allowable lower-limit granularity while associating the second granularity information with the second pathogen detector. If the communicator receives, from the information terminal, a request for the first pathogen distribution information and the first map also includes the second position, the controller may (ii-3) set, if the first predetermined granularity is equal to or higher than the second allowable lower-limit granularity, the first predetermined granularity as second display granularity for second pathogen information based on the second detection information, (ii-4) set, if the first predetermined granularity is lower than the second allowable lower-limit granularity, the second allowable lower-limit granularity as the second display granularity, and (iii) create the first pathogen distribution information by superimposing the first pathogen information in the first area and the second pathogen information in a second area, which has a size corresponding to the set second display granularity and is located at the second position on the first map.

According to this, when two pathogen detectors are provided on the first map, the display granularity for the pathogen information can be set for each of the pathogen detectors, and privacy of managers of the pathogen detectors and the like can be protected more securely.

In addition, in the pathogen distribution information provision system according to the aspect of the present disclosure, if the communicator receives, from the information terminal, a request for second pathogen distribution information on a second map on a second scale, which is different from the first scale, and the second map includes the first position, the controller may (iv) obtain second predetermined granularity corresponding to the second map, (v-1) set, if the second predetermined granularity is equal to or higher than the first allowable lower-limit granularity, the second predetermined granularity as third display granularity for the first pathogen information, (v-2) set, if the second predetermined granularity is lower than the first allowable lower-limit granularity, the first allowable lower-limit granularity as the third display granularity, and (vi) create the second pathogen distribution information by superimposing the first pathogen information in a third area, which has a third size corresponding to the set third display granularity and is located at the first position on the second map.

According to this, the first display granularity can be prevented from becoming lower than the first allowable lower-limit granularity on the second map, too, whose scale is different from that of the first map. Even when a scale of a map is variable, therefore, privacy of the managers of the pathogen detectors and the like can be protected.

In addition, in the pathogen distribution information provision system according to the aspect of the present disclosure, the controller may also evaluate, for each of the pathogen detectors on a basis of the detection information obtained by the pathogen detector, an infection risk at the position at which the pathogen detector is provided. The pathogen information may indicate results of the evaluation of the infection risks based on the corresponding detection information.

According to this, the infection risks evaluated on the basis of the detection information can be superimposed upon the map, and information more beneficial to prevention of infection can be provided.

In addition, in the pathogen distribution information provision system according to the aspect of the present disclosure, the controller may evaluate the infection risks on a basis of virus concentration detected by the pathogen detectors and a predetermined HID50 (50% human infectious dose). In addition, in the pathogen distribution information provision system according to the aspect of the present disclosure, the detection information may include humidity information at the positions at which the corresponding pathogen detectors are provided. The controller may evaluate the infection risks on a basis of absolute humidity obtained from the humidity information. In addition, in the pathogen distribution information provision system according to the aspect of the present disclosure, the controller may also obtain prevalence information regarding a disease caused by the pathogen at each of the positions at which the pathogen detectors are provided and evaluate the infection risks on a basis of the obtained prevalence level information. In addition, in the pathogen distribution information provision system according to the aspect of the present disclosure, the detection information may include congestion information, which indicates crowdedness at the positions at which the corresponding pathogen detectors are provided. The controller may evaluate the infection risks on a basis of the congestion information.

According to this, the infection risks can be evaluated on the basis of various pieces of information, which makes it possible to evaluate the infection risks more accurately.

In addition, in the pathogen distribution information provision system according to the aspect of the present disclosure, if an infection risk level indicated by each of pieces of the pathogen information is lower than a threshold level, the controller may superimpose a mark for pointing at the position of one of the pathogen detectors corresponding to the piece of the pathogen information regardless of the granularity information.

According to this, places where an infection risk is low can be indicated. Sufficient measures against infection with a pathogen, therefore, can be taken in areas in which an infection risk is high, and the places where an infection risk is low can be differentiated. As a result, an incentive to set pathogen detectors can be increased, and more detection information can be collected easily.

It should be noted that these general or specific aspects may be implemented as an apparatus, a method, an integrated circuit, a computer program, a computer-readable storage medium such as a CD-ROM, or any selective combination thereof.

Embodiments will be described hereinafter with reference to the drawings.

The embodiments described hereinafter are general or specific examples. Values, shapes, materials, components, arrangement positions and connection modes of the components, steps, order of the steps, and the like are examples, and not meant to limit the claims. In addition, among the components described in the following embodiments, ones not described in the independent claims, which define broadest concepts, will be described as optional components. In addition, the drawings are not strict illustrations. In the drawings, substantially the same components are given the same reference numerals, and redundant description thereof is omitted or simplified.

Embodiment

In a present embodiment, a case where a pathogen is influenza viruses will be described as an example. Influenza viruses might be simply referred to as viruses in the following description.

Functional Configuration of System

The functional configuration of an infection risk map provision system according to the present embodiment will be specifically described with reference to FIG. 1. FIG. 1 is a block diagram illustrating the functional configuration of the infection risk map provision system according to the embodiment.

In FIG. 1, an infection risk map provision system 10 includes virus sensors 100, an environment information database 200, an information provision server 300, one or more information terminals 400, and one or more air cleaning devices 500. The virus sensors 100, the environment information database 200, the information provision server 300, the one or more information terminals 400, and the one or more air cleaning devices 500 are connected to a communication network 600. The communication network 600 need not be particularly limited, but may be, for example, the Internet. Each of the apparatuses will be described hereinafter.

Virus Sensors

The virus sensors 100 are an example of pathogen detectors for detecting pathogens in the air, the pathogen detectors being provided at different positions. The virus sensors 100 can be provided in any kind of closed space. For example, the virus sensors 100 are provided inside public facilities (e.g., hospitals, schools, day nurseries, eldercare facilities, stations, etc.), non-public facilities (e.g., offices, stores, houses, etc.), and means of transportations (e.g., trains, buses, airplanes, automobiles, etc.). The virus sensors 100 each detect viruses in a space where the virus sensor 100 is provided.

As illustrated in FIG. 1, the virus sensors 100 each include a control unit 101, a collection unit 102, a detection unit 103, a display unit 104, a communication unit 105, and a storage unit 106.

The collection unit 102 includes a cyclone collector or a filter and collects viruses in the air.

The detection unit 103 measures virus concentration in the air by detecting viruses collected by the collection unit 102. For example, the detection unit 103 can measure virus concentration through immunochromatography. A method for detecting viruses is not limited to immunochromatography, and any method may be used.

In the present embodiment, the detection unit 103 further includes a temperature sensor, a humidity sensor, a human detection sensor, and a GPS sensor and detects temperature, humidity, and persons around the provided virus sensor 100 and a position at which the virus sensor 100 is provided. A noncontact temperature sensor that detects heat radiated by humans or an infrared sensor, for example, may be used as the human detection sensor.

The display unit 104 includes a liquid crystal display, or an organic electroluminescent (EL) display, for example, and displays information in accordance with instructions from the control unit 101.

The communication unit 105 includes, for example, a network adapter. The communication unit 105 transmits various pieces of data and receives various pieces of data from other apparatuses on the communication network 600 in accordance with instructions from the control unit 101.

The storage unit 106 includes a semiconductor memory or a hard disk drive, for example, and stores various pieces of data in accordance with instructions from the control unit 101.

The control unit 101 controls the collection unit 102, the detection unit 103, the display unit 104, the communication unit 105, and the storage unit 106. For example, the control unit 101 stores detection information, which indicates virus concentration, temperature, humidity, presence or absence or persons, and a position detected by the detection unit 103 in the storage unit 106. The control unit 101 then reads the detection information stored in the storage unit 106 at any timing and transmits the read detection information to the information provision server 300 through the communication unit 105.

The detection information transmitted to the information provision server 300 includes a virus detection result. In the present embodiment, a virus detection result is a result of classification of virus concentration using a reference value. The reference value used to classify virus concentration may be a concentration value based on, for example, a 50% human infectious dose (HID50).

The HID50 refers to the number of viruses with which 50% of persons who have inhaled infectious viruses catch influenza. For example, a value of virus concentration when the respiratory volume of an ordinary person per hour includes the number of viruses corresponding to the HID50, therefore, may be used as the reference value. When the HID50 is 300 and the respiratory volume of a person per minute is 6 liters, for example, the reference value for virus concentration is calculated as 0.83 (=300/(6×60))/liter. Because the HID50 varies depending on the size of particles including viruses, a farthest position in the body to which particles inhaled through the mouth or the nose can get, and the like, the reference value is not uniquely determined.

Virus concentration detected by the detection unit 103 is thus classified using, as the reference value, a concentration value based on the HID50 calculated in this manner. When a virus concentration value is equal to or larger than the reference value, for example, virus concentration is classified as "H", and when a virus concentration value is smaller than the reference value but larger than 0, virus concentration is classified as "L". A result of classification is transmitted to the information provision server 300 as a virus detection result.

This way of classifying virus concentration is an example, and a method for classifying virus concentration is not limited to this. For example, the reference value need not be fixed as 0.8 per liter and may be updated as necessary, instead. Alternatively, the classification may be performed by the information provision server 300. In this case, a virus detection result transmitted to the information provision server 300 may be a virus concentration value.

Environment Information Database

The environment information database 200 stores map information, influenza prevalence information, weather information, traffic and congestion information, and the like. The map information can be obtained from, for example, the Geographical Survey Institute or a cartography company. The influenza prevalence information is, for example, information indicating a degree of prevalence of influenza based on the number of patients in hospitals with influenza. The influenza prevalence information can be obtained from, for example, the National Institute of Infectious Diseases or a local government. The weather information is information indicating temperature, humidity, and a weather condition in each area and can be obtained from, for example, the Meteorological Agency or a weather news company. The traffic and congestion information is information indicating a human congestion condition and can be obtained from, for example, a transportation infrastructure-related company or personal mobile information terminals.

Information Provision Server

The information provision server 300 evaluates, on the basis of detection information obtained by the virus sensors 100, an infection risk at each position at which one of the virus sensors 100 is provided. The information provision server 300 also creates an infection risk map by superimposing infection risk information upon a map. The created infection risk map is provided for the information terminals 400.

Infection risk information is an example of pathogen information and indicates a result of evaluation of infection risks. More specifically, infection risk information indicates a probability of infection with a virus and is classified as one of three categories of "danger", "caution", and "safe" in order of the probability of infection (i.e., descending order).

An infection risk map is an example of pathogen distribution information and indicates the distribution of infection risk information. More specifically, an infection risk map is information that shows infection risk information on a map. On an infection risk map, for example, a color corresponding to infection risk information is given to each area. Correspondences between infection risk information and a color may be, for example, "danger"="red", "caution"="yellow", and "safe"="no color".

As illustrated in FIG. 1, the information provision server 300 includes a control unit 301, a communication unit 302, and a storage unit 303.

The communication unit 302 includes, for example, a network adapter. The communication unit 302 transmits various pieces of data and receives various pieces of data from the other apparatuses on the communication network 600 in accordance with instructions from the control unit 301. More specifically, the communication unit 302 collects detection information obtained by the virus sensors 100 over the communication network 600. The communication unit 302 also transmits an infection risk map to the information terminals 400 over the communication network 600.

The storage unit 303 includes a semiconductor memory or a hard disk drive, for example, and stores various pieces of data in accordance with instructions from the control unit 301. More specifically, the storage unit 303 stores collected detection information and positional information regarding the virus sensors 100 while associating the detection information and the positional information with each other.

The control unit 301 provides, for the information terminals 400 through the communication unit 302 on the basis of detection information, an infection risk map indicating the distribution of infection risk information. More specifically, the control unit 301 sets display granularity for infection risk information on the infection risk map displayed on the information terminals 400 on the basis of granularity information corresponding to the virus sensors 100.

Display granularity refers to the size of an area on a map in which infection risk information is superimposed. The coarser the display granularity, the larger the superimposition area, and the finer the display granularity, the smaller the superimposition area. When (display granularity i of infection risk information i)>(display granularity j for infection risk information j), (area i of a continuous area on a map A in which the infection risk information i is superimposed)>(area j of a continuous area on the map A or a map B, whose scale is the same as that of the map A, in which the infection risk information j is superimposed) may be established.

The control unit 301 also creates an infection risk map by superimposing the infection risk information upon the map on the basis of the set display granularity and the positional information regarding the virus sensors 100. At this time, the control unit 301 inhibits superimposition of the infection risk information in an area on the map smaller than an area on the map indicated by the granularity information. That is, an area on the map in which the infection risk information is superimposed is prevented from becoming smaller than an area on the map indicated by the granularity information.

Information Terminals

The one or more information terminals 400 are smartphones, tablet computers, or personal computers, for example, and display an infection risk map received from the information provision server 300. As illustrated in FIG. 1, the one or more information terminals 400 each include a control unit 401, an input unit 402, a display unit 403, a communication unit 404, and a storage unit 405.

The input unit 402 includes, for example, a touch panel, a mouse, or a keyboard. The input unit 402 receives an input from a user and outputs an input signal to the control unit 401. For example, the input unit 402 receives an input about a scale of the infection risk map from the user.

The display unit 403 includes, for example, a liquid crystal display or an organic EL display. The display unit 403 may be integrated with the input unit 402 as a touch display. The display unit 403 displays various pieces of information in accordance with instructions from the control unit 401. More specifically, the display unit 403 displays the infection risk map.

The communication unit 404 includes, for example, a network adapter. The communication unit 404 transmits various pieces of data and receives various pieces of data from the other apparatuses on the communication network 600 in accordance with instructions from the control unit 401. For example, the communication unit 404 transmits a message for requesting an infection risk map to the information provision server 300.

The storage unit 405 includes a semiconductor memory or a hard disk drive, for example, and stores various pieces of data in accordance with instructions from the control unit 401.

The control unit 401 transmits a message for requesting an infection risk map to the information provision server 300 through the communication unit 404 on the basis of an input signal from the input unit 402. The message includes, for example, positional information and scale information. The positional information may be obtained, for example, using a global positioning system (GPS) sensor. Furthermore, when the communication unit 404 receives an infection risk map from the information provision server 300, the control unit 401 displays the infection risk map on the display unit 403.

Air Cleaning Devices

The one or more air cleaning devices 500 each clean surrounding air. The one or more air cleaning devices 500 are, for example, air cleaners. Alternatively, the one or more air cleaning devices 500 may be devices that spray a disinfectant such as hypochlorous acid into the air. The one or more air cleaning devices 500 each receive operation condition information from the information provision server 300 and control a filter, a fan, or the like on the basis of the received operation condition information.

System Operation

Figure 2:
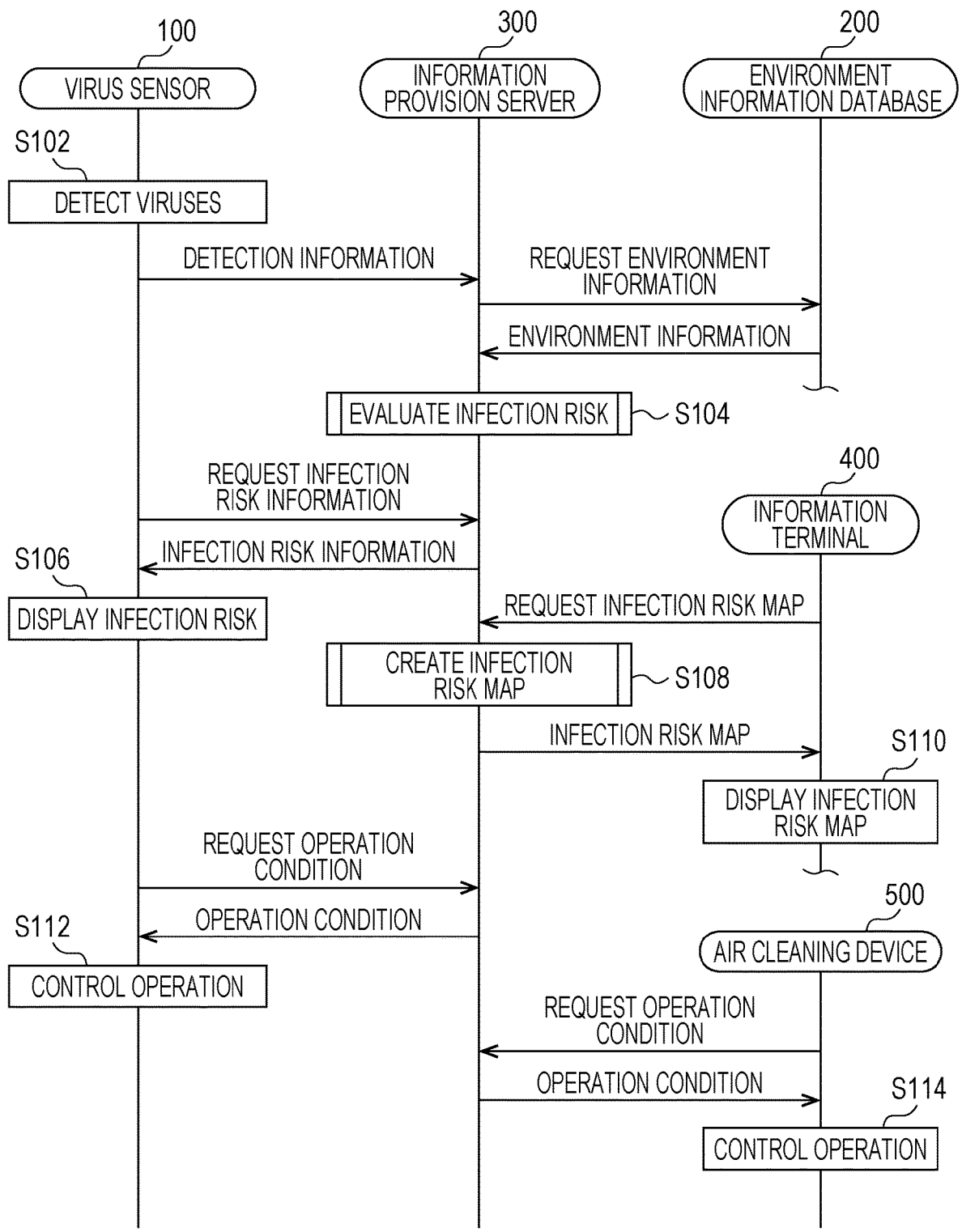
FIG. 2 is a sequence diagram of the infection risk map provision system according to the embodiment.

Next, a processing operation performed by the infection risk map provision system 10 configured as above will be specifically described with reference to the drawings. FIG. 2 is a sequence diagram of the infection risk map provision system according to the embodiment. In the following description, one of the virus sensors 100 will be referred to as the virus sensor 100, one of the one or more information terminals 400 will be referred to as the information terminal 400, and one of the one or more air cleaning devices 500 will be referred to as the air cleaning device 500.

The virus sensor 100 detects viruses and the like and transmits detection information indicating a result of the detection to the information provision server 300 (S102). FIG. 3 illustrates an example of detection information according to the embodiment.

The virus sensors 100 each have a device identifier (ID) as an identifier unique to the device. The device ID is included in detection information, and the information provision server 300 can identify a device to which detection information belongs. Date and time indicate a date and a time corresponding to detection information.

"Virus" indicates a result of classification of virus concentration measured using a concentration value based on the HID50 as a reference value. In "virus", "-" indicates that no viruses have been detected, "L" indicates that viruses less than the reference value based on the HID50 have been detected, and "H" indicates that viruses more than the reference value based on the HID50 have been detected.

"Position" indicates positional information regarding the virus sensor 100 and, more specifically, includes information regarding latitude and longitude. The positional information is detected, for example, by the GPS sensor included in the virus sensor 100. Although positional information was detected at times of "9:00" and "12:00" in FIG. 3, positional information may be detected at any timings. For example, positional information may be detected when the virus sensor 100 is set, when the virus sensor 100 is moved, or at predetermined times.

"Temperature" and "humidity" indicate Celsius temperature (atmospheric temperature) and relative humidity in a space where the virus sensor 100 is provided. The Celsius temperature and the relative humidity are detected, for example, by the temperature sensor and the humidity sensor, respectively, included in the virus sensor 100.

"Human" indicates crowdedness around the virus sensor 100 and is classified as "crowded" or "-". Crowdedness is detected, for example, by the human detection sensor included in the virus sensor 100.

Next, the information provision server 300 requests environment information from the environment information database 200 on the basis of positional information included in the detection information received from the virus sensor 100. The environment information database 200 transmits, to the information provision server 300, environment information (e.g., weather information, map information, traffic and congestion information, and influenza prevalence information) around the positional information included in the request for environment information. The information provision server 300 evaluates an infection risk on the basis of the detection information and the environment information (S104). Details of the evaluation of an infection risk will be described later with reference to FIGS. 4 and 5.

The virus sensor 100 requests infection risk information indicating a result of the evaluation of an infection risk from the information provision server 300 as necessary and receives the infection risk information from the information provision server 300. The virus sensor 100 then displays the infection risk information on the display unit 104 (S106). For example, the virus sensor 100 displays any of "danger", "caution", and "safe".

When the information provision server 300 receives a request for an infection risk map from the information terminal 400, the information provision server 300 creates an infection risk map on the basis of the infection risk information and granularity information and transmits the infection risk map to the information terminal 400 (S108). Details of the creation of an infection risk map will be described later with reference to FIGS. 6 to 14.

The information terminal 400 displays the infection risk map received from the information provision server 300 (S110).

When the information provision server 300 receives a request for an operation condition from the virus sensor 100, the information provision server 300 transmits an operation condition to the virus sensor 100 on the basis of the positional information regarding the virus sensor 100 and the infection risk map. The virus sensor 100 controls operation on the basis of the operation condition received from the information provision server 300 (S112). If a virus infection risk is high at a position at which the virus sensor 100 is provided, for example, viruses are detected at a high detection frequency. If the virus infection risk is low at a position at which the virus sensor 100 is provided, on the other hand, viruses are detected at a low detection frequency.

In addition, when the information provision server 300 receives a request for an operation condition from the air cleaning device 500, the information provision server 300 transmits an operation condition to the air cleaning device 500 on the basis of positional information regarding the air cleaning device 500 and the infection risk map. The air cleaning device 500 controls operation on the basis of the operation condition received from the information provision server 300 (S114). If a virus infection risk is high at the position at which the air cleaning device 500 is provided, for example, the air cleaning device 500 is operated on the basis of an operation condition for achieving high cleaning performance. If the virus infection risk is low at the position at which the air cleaning device 500 is provided, on the other hand, the air cleaning device 500 is operated on the basis of an operation condition for achieving low cleaning performance.

Evaluation of Infection Risk

Details of the evaluation of an infection risk will be specifically described hereinafter with reference to the drawings. FIG. 4 illustrates an example of information regarding the evaluation of an infection risk according to the embodiment.

The information illustrated in FIG. 4 includes detection information collected from the virus sensors 100, environment information received from the environment information database 200, and information generated by the information provision server 300. In FIG. 4, for example, latest detection information corresponding to each of the virus sensors 100 is managed.

"Time", "device ID", "virus", "position", "temperature", "relative humidity", and "human" are information included in the detection information collected from the virus sensors 100. These items are the same as in FIG. 3, and description thereof is omitted.

"Prevalence level" is included in the environment information received from the environment information database 200. "Prevalence level" indicates a prevalence level of influenza at a position at which a virus sensor is provided and classified as, for example, one of three categories of "none", "caution", and "warning". The prevalence level is provided for each area on the basis of, for example, the number of patients diagnosed at medical facilities with influenza.

"Absolute humidity" is calculated from "temperature" and "relative humidity" and indicates the amount of water vapor included per 1 $m^3$ of air in grams herein.

Absolute humidity is closely related to infectiousness of viruses. In G. J. Harper, "Airborne micro-organisms: survival tests with four viruses", J. Hyg., Camb. (1961), 59, 479, for example, a correlation between room temperature, relative humidity, and virus viability is demonstrated. Furthermore, in Makoto Shoji, "Correlation between seasons and influenza epidemics", J. Natl. Inst. Public Health, 48(4): 1999, a high correlation between absolute humidity and virus viability is demonstrated by analyzing data in "Airborne micro-organisms: survival tests with four viruses". In addition, according to "Correlation between seasons and influenza epidemics", a six-hour survival rate of influenza viruses with an absolute humidity of 7 $g/m^3$ is 20%, and a six-hour survival rate of influenza viruses with an absolute humidity of 5 $g/m^3$ is 50%. The virus survival rate thus tends to be high when the absolute humidity is low. That is, an infection risk is high when the absolute humidity is low.

"Allowable lower-limit granularity level" is granularity information and indicates a lower-limit level of granularity allowable as display granularity for infection risk information on an infection risk map. An allowable lower-limit granularity level corresponding to each device ID is, for example, stored in the storage unit 303 of the information provision server 300 as master data. In this case, an allowable lower-limit granularity level corresponding to a device ID included in detection information can be obtained by referring to the master data. Alternatively, for example, an allowable lower-limit granularity level may be included in detection information. In any case, granularity information (here, an allowable lower-limit granularity level) may be input by a manager of the virus sensor 100. Granularity information may be input to the virus sensor 100 when the virus sensor 100 is set or a user of the virus sensor 100 is registered, instead. Alternatively, granularity information may be input to the information provision server 300 through the information terminal 400 as necessary.

When an allowable lower-limit granularity level is input, inputting of a granularity level higher than a predetermined granularity level may be inhibited. That is, inputting of granularity coarser than predetermined granularity may be inhibited. The predetermined granularity level may be, for example, a granularity level of "3".

Here, the lower the "allowable lower-limit granularity level", the finer the granularity. Finer granularity means a smaller superimposition area. FIG. 5 illustrates an example of granularity levels according to the embodiment. When a granularity level is "1", for example, infection risk information may be superimposed within a range of a room. When a granularity level is "2", for example, infection risk information may be superimposed within a range of a building. When a granularity level is "3", for example, infection risk information may be superimposed within a range of an area. When a granularity level is "4", for example, infection risk information may be superimposed within a range of a city, a ward, a town, or a village. When a granularity level is "5", for example, infection risk information may be superimposed within a range of a prefecture.

Prefectures, cities, wards, towns, and villages are administrative districts, and sizes and positions thereof are determined in advance. Areas, buildings, and rooms, on the other hand, are circular regions whose centers are positions at which the virus sensors 100 are provided. Sizes of circular regions differ depending on the granularity level. With a granularity level of "3", for example, the radius of circles is 1 kilometer. With a granularity level of "2", for example, the radius of circles is 100 meters. With a granularity level of "1", for example, the radius of circles is 10 meters.

"Infection risk" indicates a result of evaluation of an infection risk, which will be described later. "Infection risk" is set after the evaluation of an infection risk, which will be described later.

Figure 6:
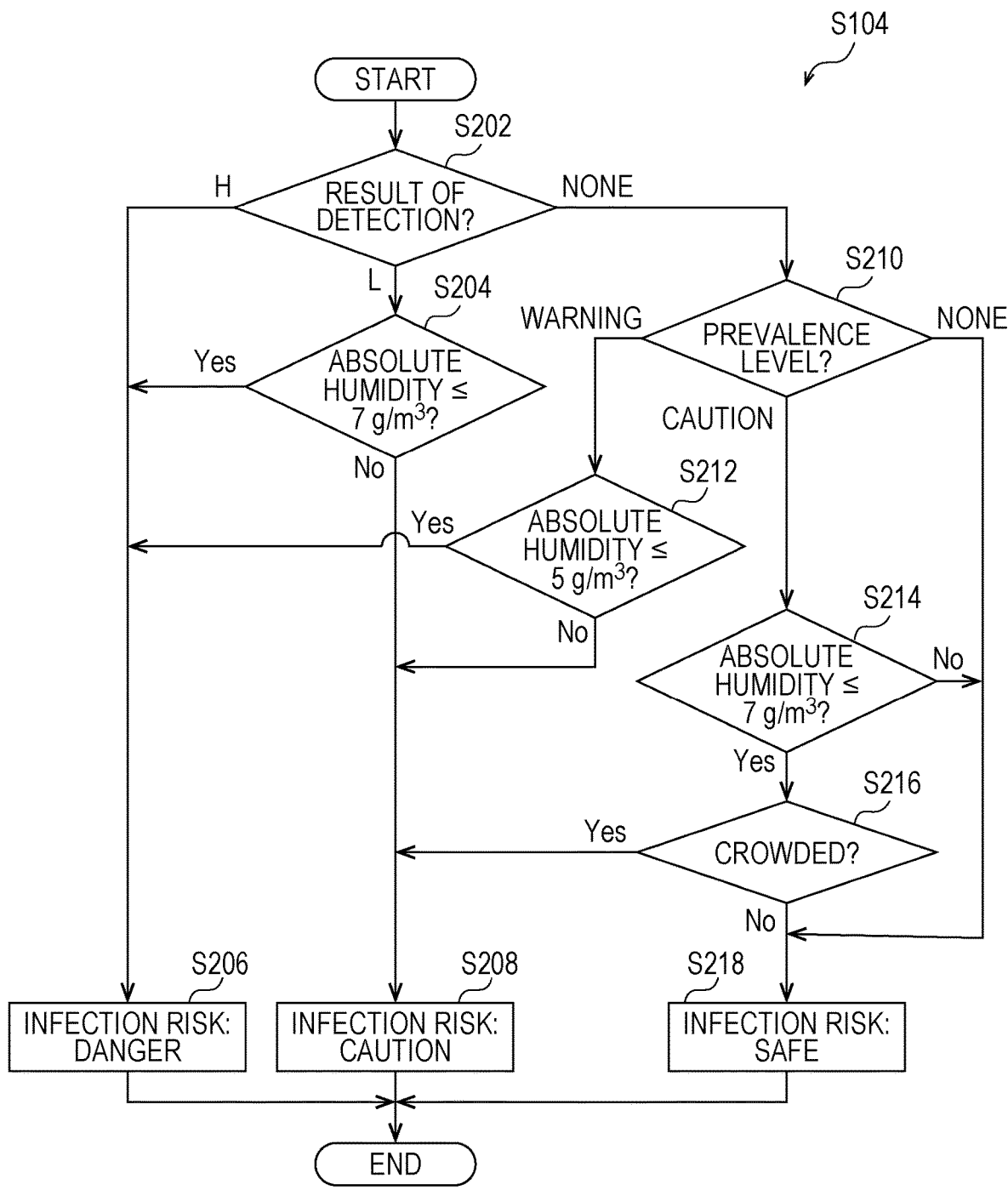
FIG. 6 is a flowchart illustrating a process for evaluating an infection risk according to the embodiment.

Now, an example of a method for evaluating an infection risk will be described with reference to FIG. 6. FIG. 6 is a flowchart illustrating a process for evaluating an infection risk according to the embodiment. The evaluation process corresponds to step S104 illustrated in FIG. 2 and is performed by the control unit 301 of the information provision server 300.

First, the control unit 301 determines whether a result of detection of viruses included in detection information is "H", "L", or "none" (S202). If the result of the detection is "L" (L in S202), the control unit 301 determines whether absolute humidity is 7 $g/m^3$ or lower (S204).

If the result of the detection is "H" (H in S202), or if absolute humidity is 7 $g/m^3$ or lower (YES in S204), the control unit 301 evaluates the infection risk as "danger" (S206).

If absolute humidity is higher than 7 $g/m^3$ (NO in S204), the control unit 301 evaluates the infection risk as "caution" (S208).

If the result of the detection is "none" (NONE in S202), the control unit 301 determines whether a prevalence level is "warning", "caution", or "none" (S210).

If the prevalence level is "warning" (WARNING in S210), the control unit 301 determines whether absolute humidity is 5 $g/m_3$ or lower (S212). If absolute humidity is 5 $g/m^3$ or lower (YES in S212), the control unit 301 evaluates the infection risk as "danger" (S206). If absolute humidity is higher than 5 $g/m^3$ (NO in S212), the control unit 301 evaluates the infection risk as "caution" (S208).

If the prevalence level is "caution" (CAUTION in S210), the control unit 301 determines whether absolute humidity is 7 $g/m^3$ or lower (S214). If absolute humidity is 7 $g/m^3$ or lower (YES in S214), the control unit 301 determines whether an area around a virus sensor is crowded (S216). If the area around the virus sensor is crowded (YES in S216), the control unit 301 evaluates the infection risk as "caution" (S208).

If the prevalence level is "none" (NONE in S210), if absolute humidity is higher than 7 $g/m^3$ (NO in S214), or if the area around the virus sensor is not crowded (NO in S216), the control unit 301 evaluates the infection risk as "safe" (S218).

Creation of Infection Risk Map

Figure 7:
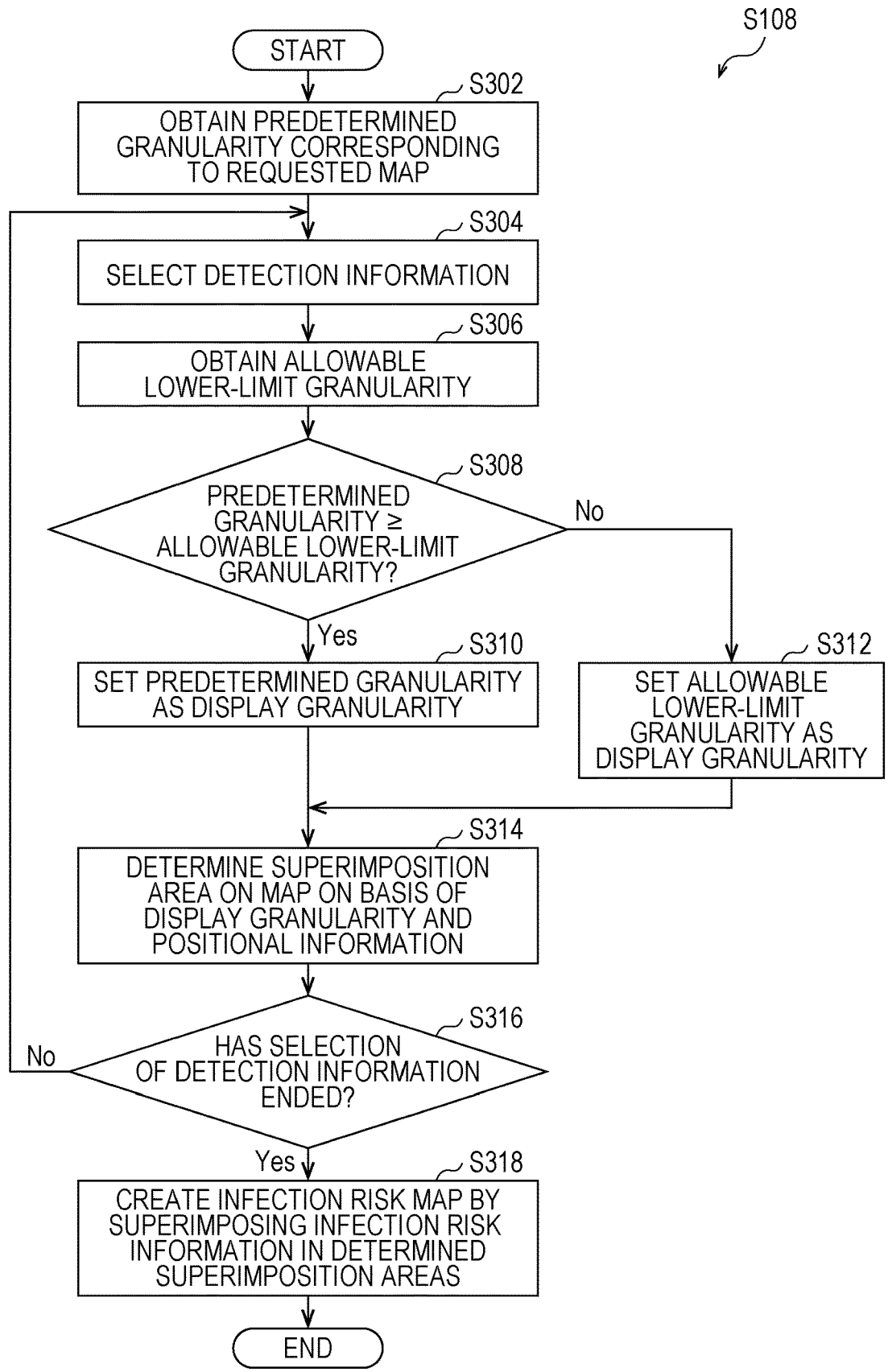
FIG. 7 is a flowchart illustrating a process for creating an infection risk map according to the embodiment.

Next, details of creation of an infection risk map will be specifically described with reference to the drawings. FIG. 7 is a flowchart illustrating a process for creating an infection risk map according to the embodiment. The creation process corresponds to step S108 illustrated in FIG. 2 and is performed by the control unit 301 of the information provision server 300.

First, the control unit 301 obtains predetermined granularity (default granularity) corresponding to a map requested by an information terminal 400 (S302). The predetermined granularity is determined in advance in accordance with, for example, a scale of the map. It is assumed, for example, that first predetermined granularity is associated with a first scale and second predetermined granularity is associated with a second scale, which is different from the first scale. If the communication unit 302 receives a request for a first infection risk map on a first map on the first scale from the information terminal 400 in this case, the control unit 301 obtains the first predetermined granularity (e.g., granularity level "1") corresponding to the first map. If the communication unit 302 receives a request for a second infection risk map on a second map on the second scale from the information terminal 400, on the other hand, for example, the control unit 301 obtains the second predetermined granularity (e.g., granularity level "3") corresponding to the second map. When a display window size of an infection risk map is variable, the predetermined granularity may depend on not only the scale but also the display window size.

The control unit 301 selects detection information including positional information on the requested map (S304). More specifically, the control unit 301 selects a data set including a "position" included on the requested map from data sets (records) illustrated, for example, in FIG. 4.

The control unit 301 obtains allowable lower-limit granularity corresponding to a virus sensor that has obtained the selected detection information (S306). When a data set including a device ID of "VS1234567" in FIG. 4 has been selected, for example, the control unit 301 obtains "1" as first allowable lower-limit granularity corresponding to a first virus sensor identified by the device ID of "VS1234567". When a data set including a device ID of "VS1323456" in FIG. 4 has been selected, on the other hand, for example, the control unit 301 obtains "3" as second allowable lower-limit granularity corresponding to a second virus sensor identified by the device ID of "VS1323456".

The control unit 301 compares the predetermined granularity with the allowable lower-limit granularity (S308). If the predetermined granularity is equal to or higher than the allowable lower-limit granularity (Yes in S308), the control unit 301 sets the predetermined granularity as display granularity for infection risk information (S310). If the predetermined granularity is lower than the allowable lower-limit granularity, on the other hand, the control unit 301 sets the allowable lower-limit granularity as the display granularity for infection risk information (S312).

It is assumed, for example, that a request for the first infection risk map on the first map has been received from an information terminal 400. Here, if the data set including the device ID of "VS1234567" in FIG. 4 has been selected, the first predetermined granularity "1" corresponding to the first map is equal to or higher than the first allowable lower-limit granularity "1". The control unit 301, therefore, sets the first predetermined granularity "1" as first display granularity for first infection risk information "caution". If the data set including the device ID of "VS1323456" in FIG. 4 has been selected, on the other hand, the first predetermined granularity "1" is lower than the second allowable lower-limit granularity "3". The control unit 301, therefore, sets the second lower-limit granularity "3" as second display granularity for second infection risk information "danger".

It is also assumed, for example, that a request for the second infection risk map on the second map has been received from an information terminal 400. Here, if the data set including the device ID of "VS1234567" in FIG. 4 has been selected, the second predetermined granularity "3" corresponding to the second map is equal to or higher than the first allowable lower-limit granularity "1". The control unit 301, therefore, sets the second predetermined granularity "3" as the first display granularity for the first infection risk information "caution". If the data set including the device ID of "VS1323456" in FIG. 4 has been selected, on the other hand, the second predetermined granularity "3" is equal to or higher than the second allowable lower-limit granularity "3". The control unit 301, therefore, sets the second lower-limit granularity "3" as the second display granularity for the second infection risk information "danger".

The control unit 301 determines, on the basis of the set display granularity and the positional information, an area in which the infection risk information is to be superimposed (S314). The size of the superimposition area depends on the display granularity. More specifically, the size of the superimposition area increases as the display granularity becomes coarser (i.e., as the granularity level increases). Conversely, the size of the superimposition area decreases as the display granularity becomes finer (i.e., as the granularity level decreases). A position of the superimposition area depends on the positional information corresponding to the selected detection information. More specifically, the superimposition area includes a position on the map identified by latitude and longitude included in the selected data set.

The control unit 301 determines whether selection of detection information has ended (S316). For example, the control unit 301 determines whether all pieces of detection information associated with the positional information included on the requested map have been selected. Here, if the control unit 301 determines that the selection of detection information has not ended (No in S316), the process returns to step S304. If determining that the selection of detection information has ended (Yes in S316), on the other hand, the control unit 301 creates an infection risk map by superimposing infection risk information corresponding to virus sensors provided on the requested map in the determined superimposition areas (S318).

Specific examples of the infection risk map created in this manner will be described with reference to FIGS. 8 to 14. In FIGS. 8 to 14, hatching is used instead of colors.

Each of FIGS. 8 to 12 illustrates an example of an infection risk map at a time when a granularity level "1" is set as the allowable lower-limit granularity. In FIGS. 8 to 12, the granularity level "1" is set for every virus sensor as the allowable lower-limit granularity.

Figure 8:
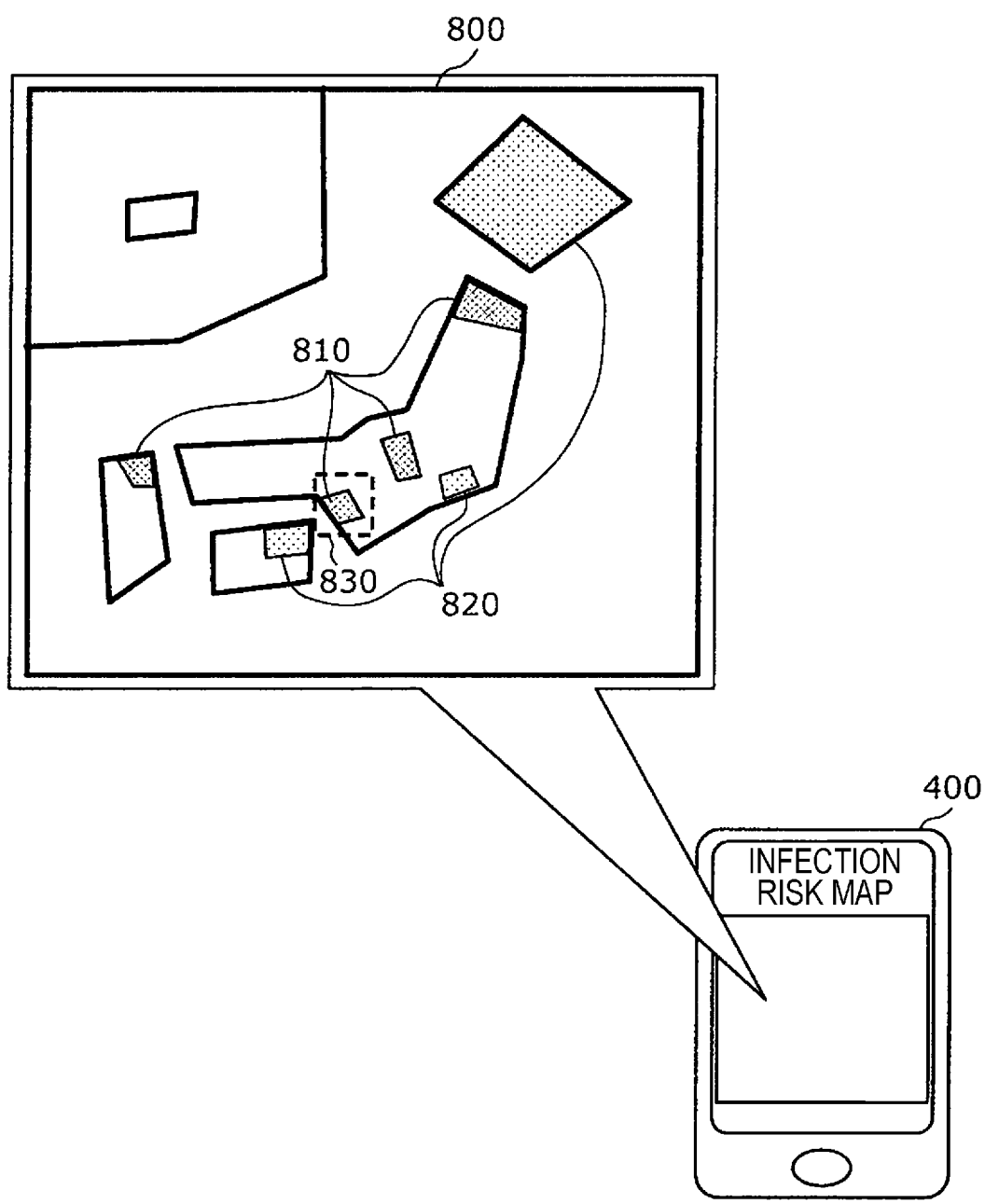
FIG. 8 is a diagram illustrating an example of an infection risk map at a time when a granularity level "1" is set as an allowable lower-limit granularity.

An infection risk map 800 illustrated in FIG. 8 is a small-scale map including the entirety of Japan and has a scale of, say, 1/1,000,000. Here, a predetermined granularity level for the infection risk map 800 is "5". In this case, since the predetermined granularity level "5" is equal to or higher than the allowable lower-limit granularity level, display granularity for infection risk information is set at the predetermined granularity level "5".

Areas 810 on the infection risk map 800 in which dense hatching is provided are areas in which "danger" is superimposed as the infection risk information. Areas 820 in which sparse hatching is provided are areas in which "caution" is superimposed as the infection risk information. Sizes of the areas 810 and 820 correspond to the granularity level "5" (here, a prefecture) set as the display granularity.

If an input for expanding an area 830 is made on the infection risk map 800, an information terminal 400 requests an infection risk map on a larger scale from the information provision server 300. As a result, an infection risk map 900 illustrated in FIG. 9 is created and transmitted to the information terminal 400.

Figure 9:
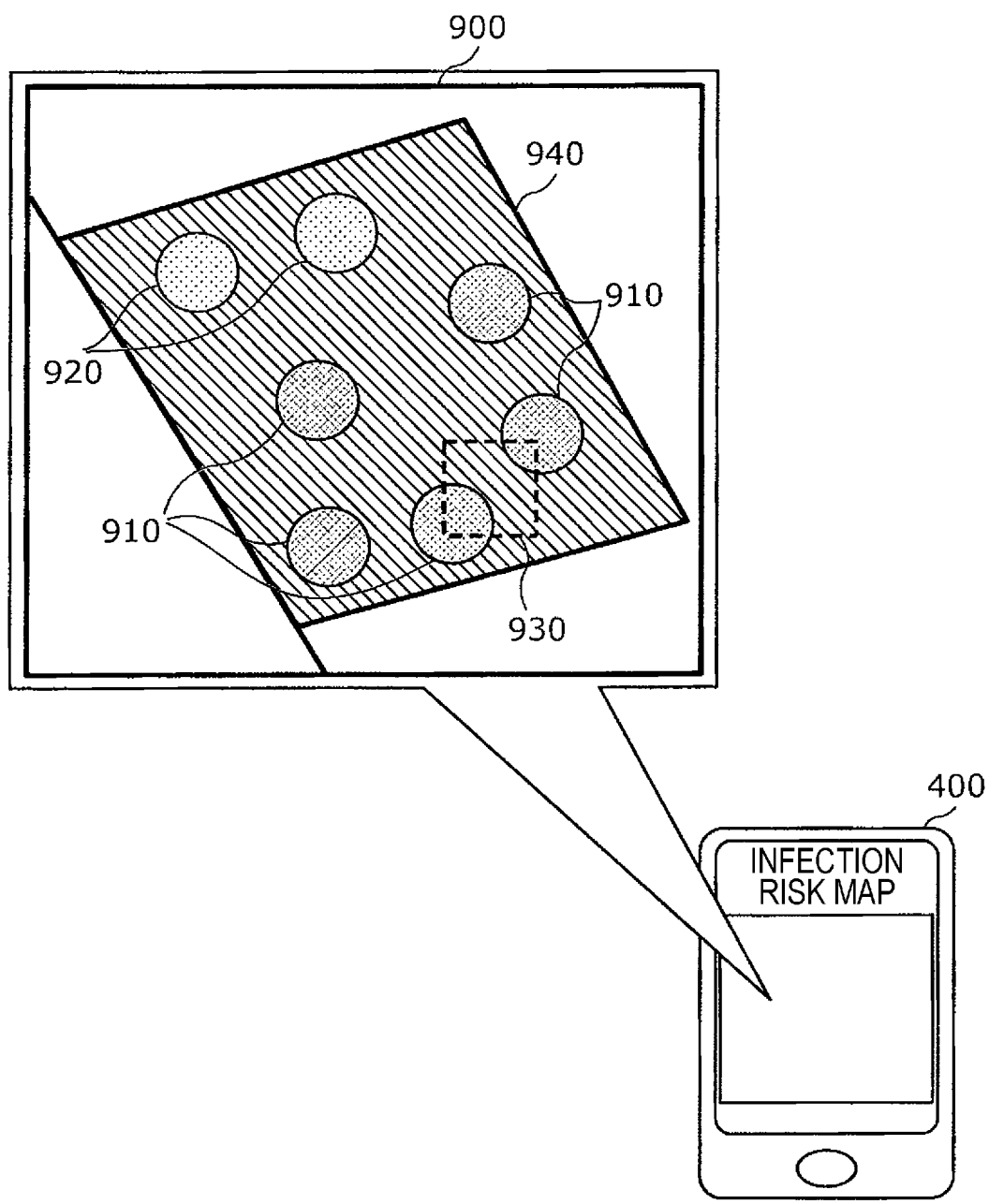
FIG. 9 is a diagram illustrating another example of the infection risk map at a time when the granularity level "1" is set as the allowable lower-limit granularity.

The infection risk map 900 illustrated in FIG. 9 is a small-scale or middle-scale map including the area 830 illustrated in FIG. 8 and has a scale of, say, 1/100,000. Here, a predetermined granularity level for the infection risk map 900 is "4". In this case, since the predetermined granularity level "4" is equal to or higher than the allowable lower-limit granularity level "1", the display granularity for the infection risk information is set at the predetermined granularity level "4".

Areas 910 on the infection risk map 900 in which dense hatching is provided are areas in which "danger" is superimposed as the infection risk information. Areas 920 in which sparse hatching is provided are areas in which "caution" is superimposed as the infection risk information. Sizes of the areas 910 and 920 correspond to the granularity level "4" (here, a city, a ward, a town, or a village) set as the display granularity. Hatching provided for an area 940 represents a prevalence level.

If an input for expanding an area 930 is made on the infection risk map 900, the information terminal 400 requests an infection risk map on a larger scale from the information provision server 300. As a result, an infection risk map 1000 illustrated in FIG. 10 is created and transmitted to the information terminal 400.

Figure 10:
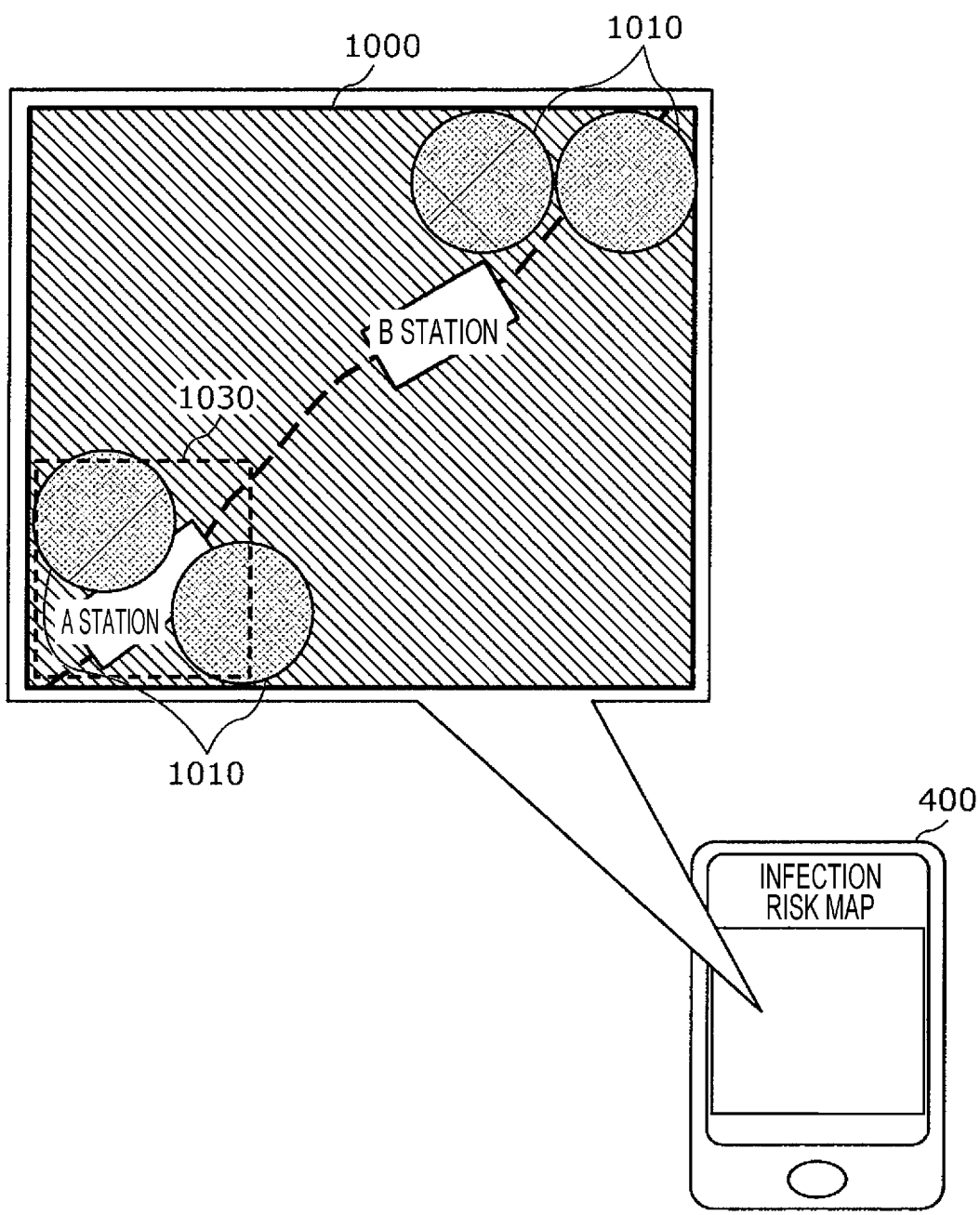
FIG. 10 is a diagram illustrating another example of the infection risk map at a time when the granularity level "1" is set as the allowable lower-limit granularity.

The infection risk map 1000 illustrated in FIG. 10 is a middle-scale map including the area 930 illustrated in FIG. 9 and has a scale of, say, 1/25,000. Here, a predetermined granularity level for the infection risk map 1000 is "3". In this case, since the predetermined granularity level "3" is equal to or higher than the allowable lower-limit granularity level "1", the display granularity for the infection risk information is set at the predetermined granularity level "3".

Areas 1010 on the infection risk map 1000 in which hatching is provided are areas in which "danger" is superimposed as the infection risk information. A size of the areas 1010 corresponds to the granularity level "3" (here, an area) set as the display granularity. Hatching provided over the infection risk map 1000 represents a prevalence level.

If an input for expanding an area 1030 is made on the infection risk map 1000, the information terminal 400 requests an infection risk map on a larger scale from the information provision server 300. As a result, an infection risk map 1100 illustrated in FIG. 11 is created and transmitted to the information terminal 400.

Figure 11:
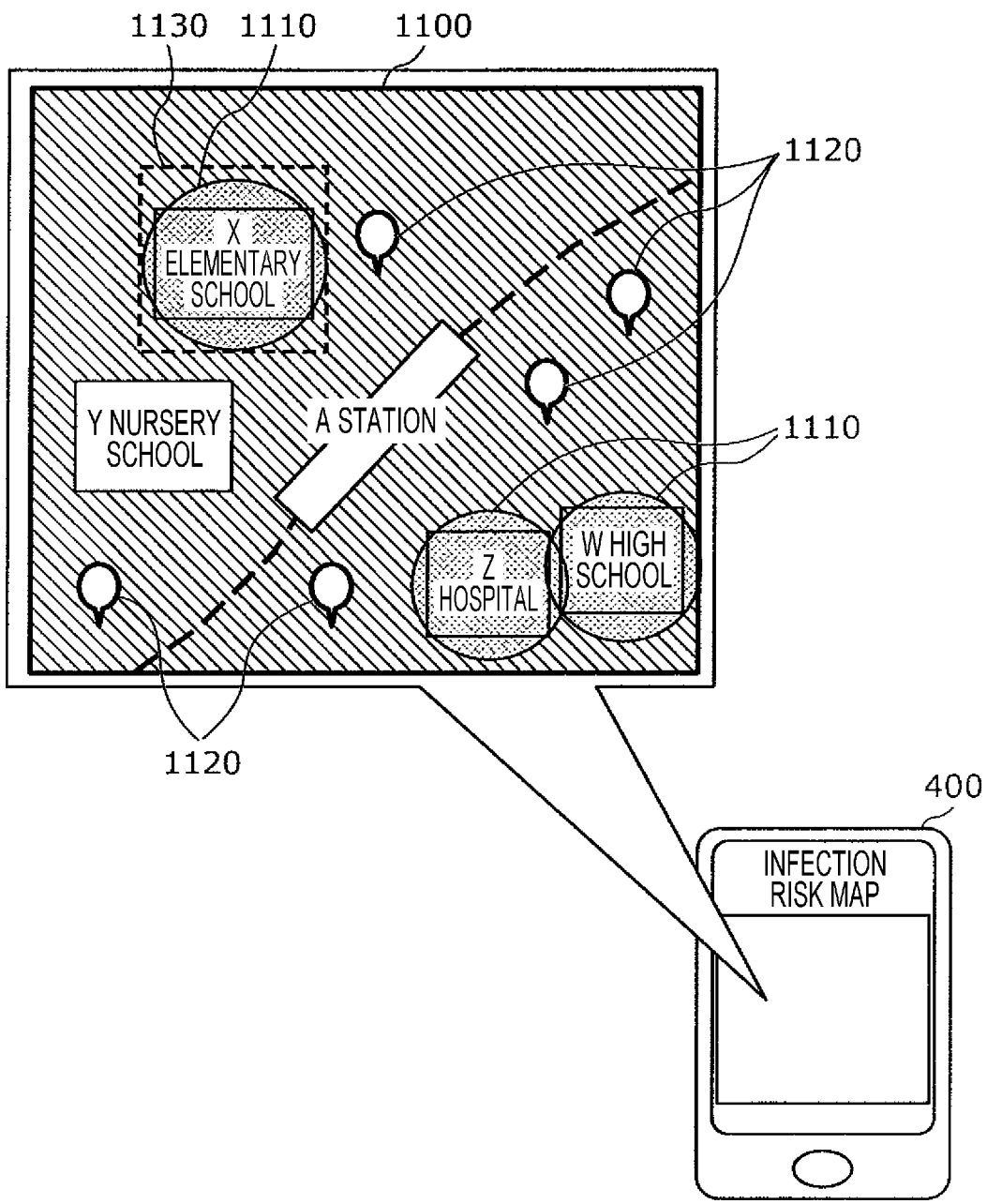
FIG. 11 is a diagram illustrating another example of the infection risk map at a time when the granularity level "1" is set as the allowable lower-limit granularity.

The infection risk map 1100 illustrated in FIG. 11 is a middle-scale or a large-scale map including the area 1030 illustrated in FIG. 10 and has a scale of, say, 1/10,000. Here, a predetermined granularity level for the infection risk map 1100 is "2". In this case, since the predetermined granularity level "2" is equal to or higher than the allowable lower-limit granularity level "1", the display granularity for the infection risk information is set at the predetermined granularity level "2".

Areas 1110 on the infection risk map 1100 in which hatching is provided are areas in which "danger" is superimposed as the infection risk information. A size of the areas 1110 corresponds to the granularity level "2" (here, a building) set as the display granularity. Hatching provided over the infection risk map 1100 represents a prevalence level.

Pin marks 1120 indicate that an infection risk level is lower than a threshold level. Here, "caution" is used as the threshold level. That is, the pin marks 1120 point at positions where an infection risk level has been evaluated as "safe".

If an input for expanding an area 1130 is made on the infection risk map 1100, the information terminal 400 requests an infection risk map on a larger scale from the information provision server 300. As a result, an infection risk map 1200 illustrated in FIG. 12 is created and transmitted to the information terminal 400.

Figure 12:
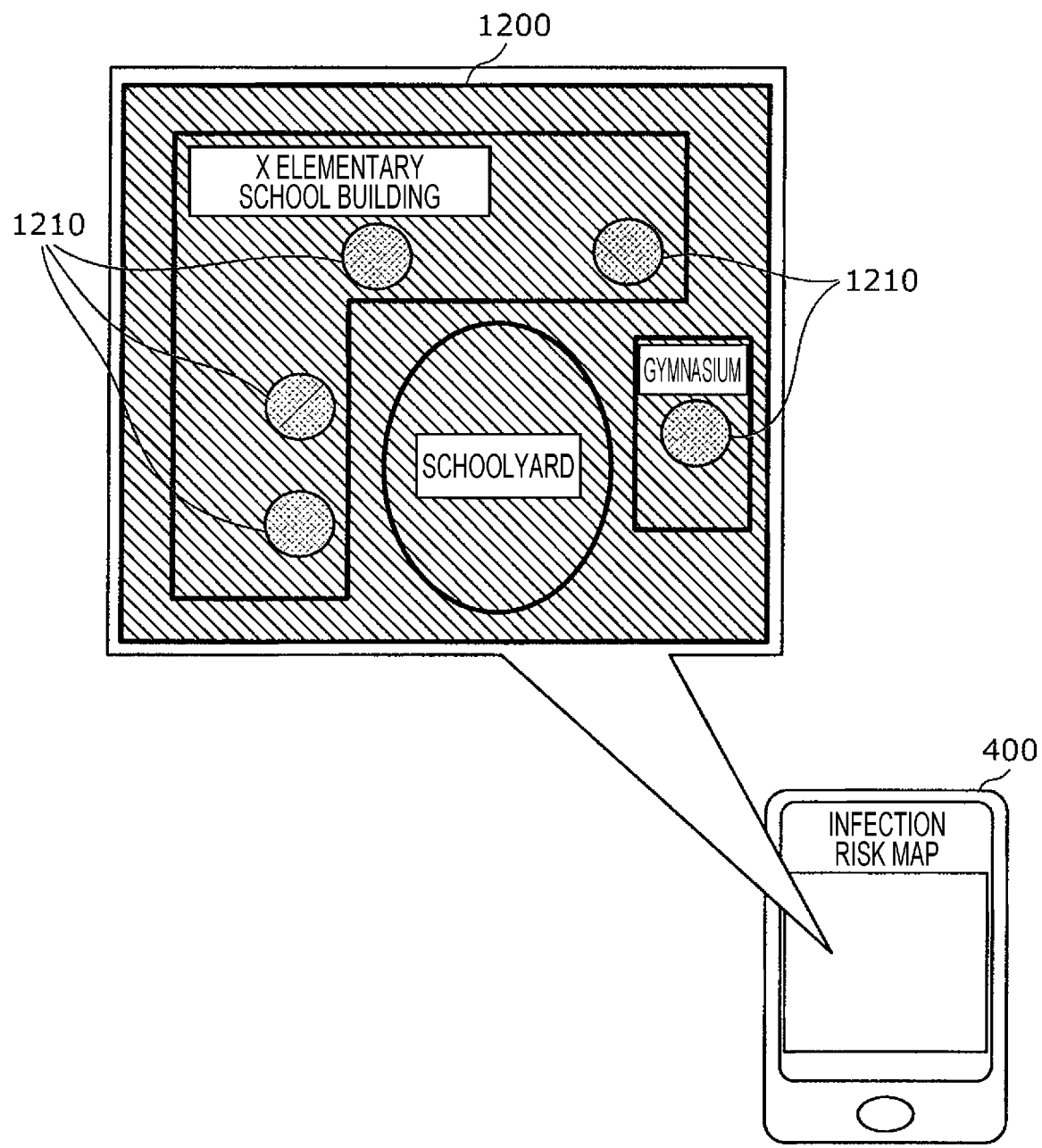
FIG. 12 is a diagram illustrating another example of the infection risk map at a time when the granularity level "1" is set as the allowable lower-limit granularity.

The infection risk map 1200 illustrated in FIG. 12 is a large-scale map including the area 1130 illustrated in FIG. 11 and has a scale of, say, 1/2,500. Here, a predetermined granularity level for the infection risk map 1200 is "1". In this case, since the predetermined granularity level "1" is equal to or higher than the allowable lower-limit granularity level "1", the display granularity for the infection risk information is set at the predetermined granularity level "1".

Areas 1210 on the infection risk map 1200 in which hatching is provided are areas in which "danger" is superimposed as the infection risk information. A size of the areas 1210 corresponds to the granularity level "1" (here, a room) set as the display granularity. Hatching provided over the infection risk map 1200 represents a prevalence level.

As described above, since a lowest granularity level "1" is set for every virus sensor as the allowable lower-limit granularity in FIGS. 8 to 12, the predetermined granularity corresponding to the maps is employed as the display granularity.

A case where a granularity level "3" is set for every virus sensor as the allowable lower-limit granularity will be described hereinafter with reference to FIGS. 13 and 14. Each of FIGS. 13 and 14 illustrates an example of an infection risk map at a time when a granularity level "3" is set as the allowable lower-limit granularity.

Infection risk maps corresponding to predetermined granularity levels "1" to "3" are the same as in FIGS. 8 to 10, where a granularity level "1" is set as the allowable lower-limit granularity, and illustration and description thereof is omitted.

Figure 13:
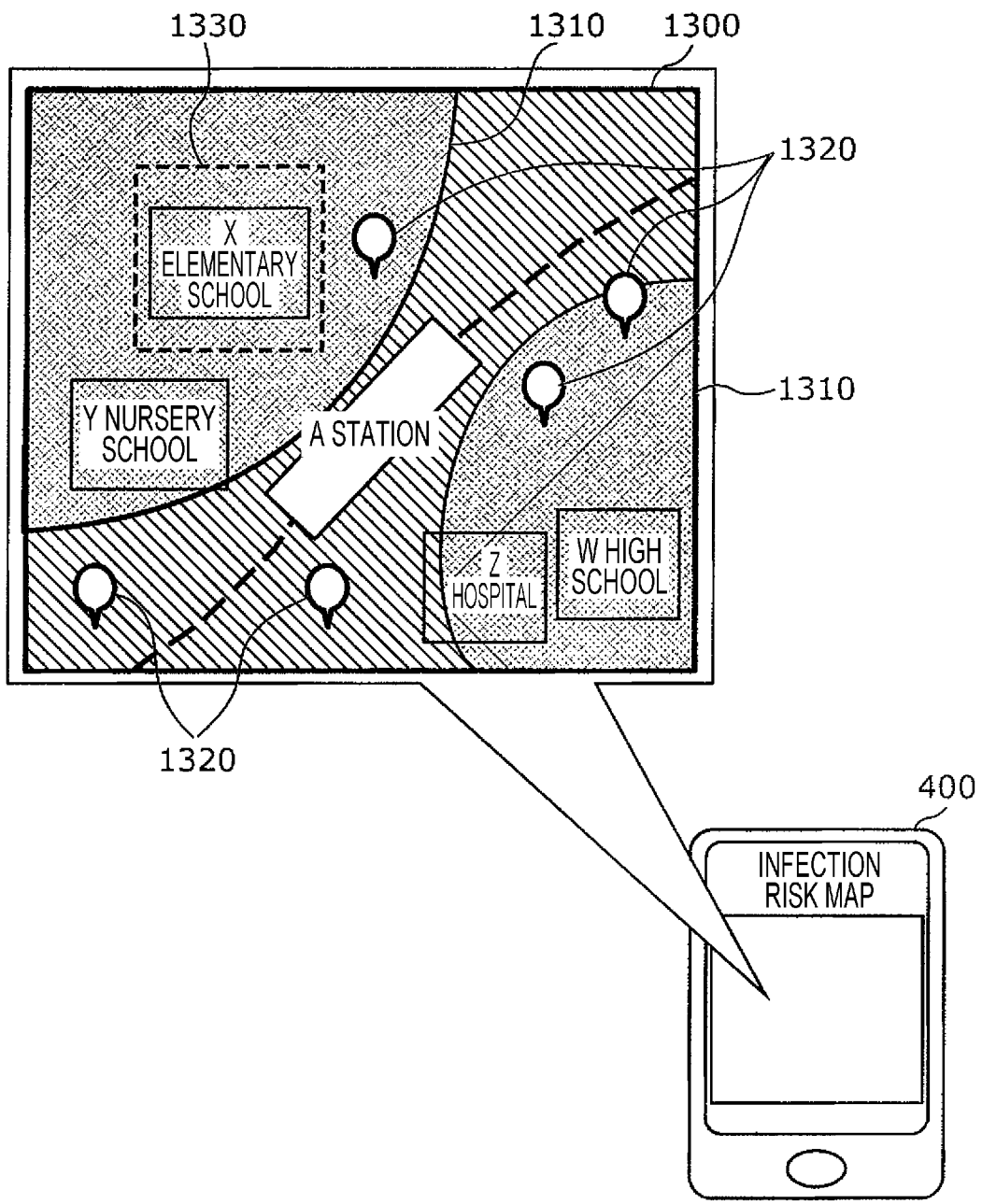
FIG. 13 is a diagram illustrating an example of an infection risk map at a time when a granularity level "3" is set as the allowable lower-limit granularity.
Figure 14:
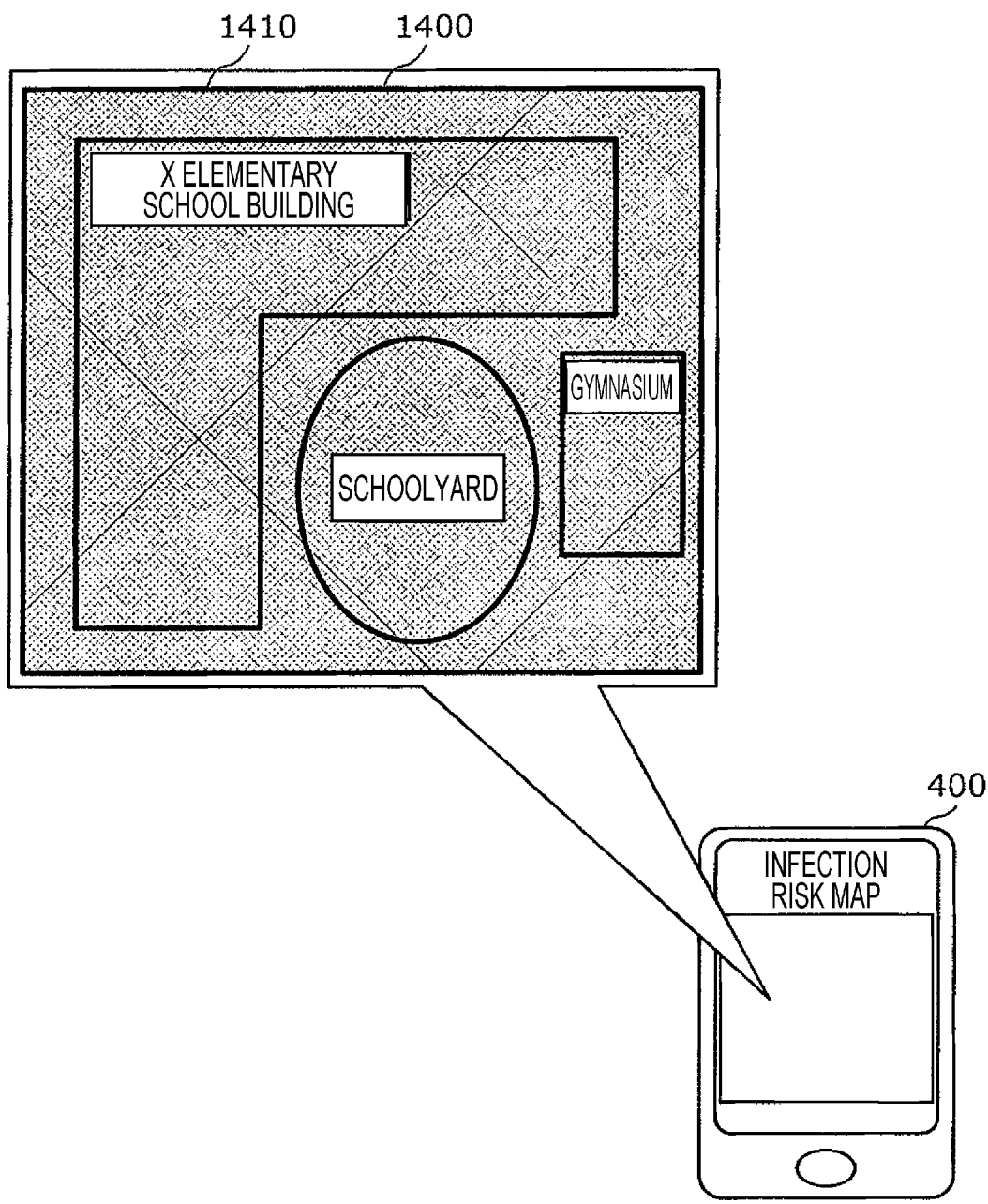
FIG. 14 is a diagram illustrating another example of the infection risk map at a time when the granularity level "3" is set as the allowable lower-limit granularity.

An infection risk map 1300 illustrated in FIG. 13 is a middle-scale or large-scale map including, as with FIG. 11, the area 1030 illustrated in FIG. 10 and has a scale of, say, 1/10,000. Here, a predetermined granularity level for the infection risk map 1300 is "2". In this case, since the predetermined granularity level "2" is lower than the allowable lower-limit granularity level "3", the display granularity for the infection risk information is set at the allowable lower-limit granularity level "3".

Areas 1310 on the infection risk map 1300 in which hatching is provided are areas in which "danger" is superimposed as the infection risk information. A size of the areas 1310 corresponds to the granularity level "3" (here, an area) set as the display granularity.

Pin marks 1320 indicate that an infection risk level is lower than a threshold level. Here, "caution" is used as the threshold level. That is, the pin marks 1320 point at positions where an infection risk level has been evaluated as "safe".

If an input for expanding an area 1330 is made on the infection risk map 1300, the information terminal 400 requests an infection risk map on a larger scale from the information provision server 300. As a result, an infection risk map 1400 illustrated in FIG. 14 is created and transmitted to the information terminal 400.

The infection risk map 1400 illustrated in FIG. 14 is a large-scale map including, as with FIG. 12, the area 1330 illustrated in FIG. 13 and has a scale of, say, 1/2,500. Here, a predetermined granularity level for the infection risk map 1300 is "1". In this case, since the predetermined granularity level "1" is lower than the allowable lower-limit granularity level "3", the display granularity for the infection risk information is set at the allowable lower-limit granularity level "3".

An area 1410 on the infection risk map 1400 in which hatching is provided is an area in which "danger" is superimposed as the infection risk information. A size of the area 1410 corresponds to the granularity level "3" (i.e., an area)

set as the display granularity. The area 1410, therefore, covers the entirety of the infection risk map 1400.

Effects, etc.

As described above, with the infection risk map provision system 10 according to the present embodiment, detection information obtained by the virus sensors 100 can be collected, and an infection risk map representing the distribution of infection risk information can be provided for the information terminals 400 on the basis of the detection information. The infection risk map, therefore, can reflect virus information more promptly than a conventional influenza prevalence level map, which does not obtain information until patients with influenza see a doctor. Consequently, information beneficial to prevention of infection from not only patients who have developed symptoms but also patients who have not developed symptoms yet can be provided, and information beneficial to prevention of infection can be provided promptly.

Furthermore, with the infection risk map provision system 10 according to the present embodiment, display granularity for each piece of infection risk information on an infection risk map can be set on the basis of granularity information corresponding to each of the virus sensors 100. Display granularity for infection risk information, therefore, can be adjusted for each virus sensor. That is, when a manager of a virus sensor does not desire a position at which the virus sensor is provided to be identified from the infection risk map, display granularity for infection risk information corresponding to the virus sensor can be made coarse in order to protect privacy of the manager of the virus sensor and the like.

For example, a manager (e.g., a person who owns a restaurant or a retail store) who does not desire a position at which a virus sensor 100 is provided to be identified can prevent identification of a location of a store at which an infection risk is high and reduction in the number of customers by setting a granularity level "3" as the allowable lower-limit granularity level. In addition, a manager (e.g., a person who owns a store in which an air cleaning device is installed) who desires to use safety as a selling point can expect an increase in the number of customers by setting a granularity level "1" as the allowable lower-limit level and making it possible to identify a store at which an infection risk is low. By inhibiting setting of a granularity level higher than a predetermined granularity level when the allowable lower-limit granularity level is set, infection risk information can be prevented from being provided with granularity that is too coarse and a decrease in value for prevention of infection can be suppressed.

Other Embodiments

Although the infection risk map provision system 10 according to one or more aspects of the present disclosure has been described above on the basis of an embodiment, the present disclosure is not limited to the embodiment. Modes obtained by modifying the present embodiment in various ways conceivable by those skilled in the art may also be included in the one or more aspects of the present disclosure insofar as the scope of the present disclosure is not deviated from.

For example, the control units 101, 301, and 401 in the above embodiment may each be achieved by a dedicated electronic circuit. The dedicated electronic circuit may be integrated on a single chip or formed on different chips. Alternatively, the control units 101, 301, and 401 may each be achieved by a general-purpose processor and a memory storing a software program or an instruction. In this case, the processor functions as the control unit 101, 301, or 401 when the software program or the instruction is executed.

Although a case where the pathogen is influenza viruses has been described in the above embodiment, the pathogen is not limited to influenza viruses. For example, the above system can be employed for other viruses, fungi, bacteria, pollen, PM2.5, and the like in the same way as for influenza viruses.

Although infection risk information is superimposed upon a map in the above embodiment, information superimposed is not limited to infection risk information. For example, virus information indicating a result of detection of viruses may be superimposed upon a map, instead.

Although a case where areas in which infection risk information is superimposed overlap with each other has not been specifically described in the above embodiment, when superimposition areas overlap with each other, a representative value of infection risk information may be used in an overlap area. As the representative value, for example, an average, a maximum value, a minimum value, or a median may be used.

The present disclosure can be used for an infection risk map provision system that provides an infection risk map that visually represents a risk of being infected with influenza.

What is claimed is:

1. A system comprising:
    a pathogen detector that measures virus concentration in air, the pathogen detector being provided at a position;
    a communicator that collects, over a communication network, detection information provided by the pathogen detector, the detection information including positional information indicating the position and information indicating a result of classification of the virus concentration;
    a storage that stores the collected detection information; and
    a controller that generates a map on a basis of the detection information stored in the storage,
    wherein the map has a scale and a location indicating a probability of infection, the location including the position and having an area,
    wherein the area has a first size when predetermined granularity corresponding to the scale is equal to or bigger than granularity information corresponding to the pathogen detector, thereby the area having a first size being distinguished in the map,
    wherein the area has a second size when the predetermined granularity is smaller than the granularity information, thereby the area having the second size not being distinguished in the map, and
    wherein the first size is smaller than the second size.

2. A pathogen distribution information provision system comprising:
    pathogen detectors for measuring virus concentrations in air, the pathogen detectors being provided at different positions;
    a communicator that collects, over a communication network, detection information obtained by the pathogen detectors, the detection information including positional information indicating the different positions and information indicating a result of classification of the virus concentrations;
    a storage that stores the collected detection information; and
    a controller that provides pathogen distribution information indicating distribution of pathogen information for an information terminal through the communicator on a basis of the detection information stored in the storage, wherein the controller displays the pathogen distribution information on the information terminal;

sets, on a basis of granularity information corresponding to the pathogen detectors, display granularity for the pathogen information in the pathogen distribution information displayed on the information terminal, and creates the pathogen distribution information by superimposing the pathogen information upon a map on a basis of the set display granularity and the positional information, wherein, in the creation of the pathogen distribution information, the controller inhibits, for the pathogen information, superimposition of the pathogen information upon the map in an area having a size smaller than a size of an area on the map indicated by the granularity information, wherein the pathogen detectors include a first pathogen detector provided at a first position, wherein the detection information includes first detection information obtained by the first pathogen detector, wherein the storage stores first granularity information indicating first allowable lower-limit granularity while associating the first granularity information with the first pathogen detector, and wherein, if the communicator receives, from the information terminal, a request for first pathogen distribution information on a first map on a first scale and the first map includes the first position, the controller (i) obtains first predetermined granularity corresponding to the first map, (ii-1) sets, if the first predetermined granularity is equal to or higher than the first allowable lower-limit granularity, the first predetermined granularity as first display granularity for first pathogen information based on the first detection information, (ii-2) sets, if the first predetermined granularity is lower than the first allowable lower-limit granularity, the first allowable lower-limit granularity as the first display granularity, and (iii) creates the first pathogen distribution information by superimposing the first pathogen information in a first area, which has a first size corresponding to the set first display granularity and is located at the first position on the first map.

3. The pathogen distribution information provision system according to claim 2, wherein the pathogen detectors further include a second pathogen detector provided at a second position, wherein the detection information includes second detection information obtained by the second pathogen detector, wherein the storage also stores second granularity information indicating second allowable lower-limit granularity while associating the second granularity information with the second pathogen detector, and wherein, if the communicator receives, from the information terminal, a request for the first pathogen distribution information and the first map also includes the second position, the controller (ii-3) sets, if the first predetermined granularity is equal to or higher than the second allowable lower-limit granularity, the first predetermined granularity as second display granularity for second pathogen information based on the second detection information, (ii-4) sets, if the first predetermined granularity is lower than the second allowable lower-limit granularity, the second allowable lower-limit granularity as the second display granularity, and (iii) creates the first pathogen distribution information by superimposing the first pathogen information in the first area and the second pathogen information in a second area, which has a second size corresponding to the set second display granularity and is located at the second position on the first map.

4. The pathogen distribution information provision system according to claim 2, wherein, if the communicator receives, from the information terminal, a request for second pathogen distribution information on a second map on a second scale, which is different from the first scale, and the second map includes the first position, the controller (iv) obtains second predetermined granularity corresponding to the second map, (v-1) sets, if the second predetermined granularity is equal to or higher than the first allowable lower-limit granularity, the second predetermined granularity as third display granularity for the first pathogen information, (v-2) sets, if the second predetermined granularity is lower than the first allowable lower-limit granularity, the first allowable lower-limit granularity as the third display granularity, and (vi) creates the second pathogen distribution information by superimposing the first pathogen information in a third area, which has a third size corresponding to the set third display granularity and is located at the first position on the second map.

5. The system according to claim 1, wherein the controller evaluates, on a basis of the detection information provided obtained by the pathogen detector, an infection risk at the position, and wherein the map indicates a result of the evaluation of the infection risk.

6. The system according to claim 5, wherein the controller evaluates the infection risk on a basis of virus concentration detected by the pathogen detector and a predetermined HID50, the HID50 being 50% human infectious dose.

7. The pathogen distribution information provision system according to claim 5, wherein the detection information includes humidity information at the position, and wherein the controller evaluates the infection risk on a basis of absolute humidity obtained from the humidity information.

8. The system according to claim 5, wherein the controller obtains prevalence information regarding a disease caused by the pathogen at the position, and evaluates the infection risk on a basis of the obtained prevalence level information.

9. The system according to claim 5, wherein the detection information includes congestion information, which indicates crowdedness at the position, and wherein the controller evaluates the infection risky risk on a basis of the congestion information.

10. The pathogen distribution information provision system according to claim 5, wherein, if an infection risk level indicated by of the map is lower than a threshold level, the controller superimposes a mark for pointing at the position regardless of the granularity information.

11. A server comprising:
a communicator that collects, over a communication network, detection information provided by a pathogen detector that measures virus concentration in air, the pathogen detector being provided at a position, the detection information including positional information indicating the position and information indicating a result of classification of the virus concentration;
a storage that stores the collected detection information; and
a controller that generates a map pathogen information on a basis of the detection information stored in the storage,
wherein the map has a scale and a location indicating a probability of infection, the location including the position and having an area,
wherein the area has a first size when predetermined granularity corresponding to the scale is equal to or bigger than granularity information corresponding to the pathogen detector, thereby the area having a first size being distinguished in the map,
wherein the area has a second size when the predetermined granularity is smaller than the granularity information, thereby the area having the second size not being distinguished in the map, and
wherein the first size is smaller than the second size.

12. A method comprising:
measuring a virus concentration in air using a pathogen detector provided at a position ;
collecting, over a communication network, detection information provided by the pathogen detector, the detection information including positional information indicating the position and information indicating a result of classification of the virus concentration;
storing the collected detection information; and
generating a map on a basis of the detection information,
wherein the map has a scale and a location indicating a probability of infection, the location including the position and having an area,
wherein the area has a first size when predetermined granularity corresponding to the scale is equal to or bigger than granularity information corresponding to the pathogen detector, thereby the area having a first size being distinguished in the map,
wherein the area has a second size when the predetermined granularity is smaller than the granularity information, thereby the area having the second size not being distinguished in the map, and
wherein the first size is smaller than the second size.

13. The system according to claim 1, wherein a size value of the granularity information corresponding to the pathogen detector is selectively input by a manager of the pathogen detector to result in the position of the pathogen detector to either be identified or not identified from the map based on the size value that was selectively input by the manager.

14. The system according to claim 1, wherein a size value of the granularity information corresponding to the pathogen detector is stored in the storage and is utilized to result in the position of the pathogen detector to either be identified or not identified from the map based on the size value of the granularity information that was obtained from the storage.

* * * * *